United States Patent
Jolliffe et al.

(10) Patent No.: US 6,593,474 B1
(45) Date of Patent: Jul. 15, 2003

(54) ARYLSUBSTITUTED PIPERAZINES USEFUL IN THE TREATMENT OF BENIGN PROSTATIC HYPERPLASIA

(75) Inventors: Linda Jolliffe, Belle Mead, NJ (US); William Murray, Belle Mead, NJ (US); Virginia Pulito, Flemington, NJ (US); Linda Mulcahy, Flemington, NJ (US); Xiaobing Li, San Diego, CA (US); Allen Reitz, Lansdale, PA (US); Cynthia Maryanoff, Forest Grove, PA (US); Frank Villani, Perkasie, PA (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 0 days.

(21) Appl. No.: 09/591,814

(22) Filed: Jun. 12, 2000

Related U.S. Application Data

(62) Division of application No. 09/526,224, filed on Mar. 15, 2000, now Pat. No. 6,303,594, which is a continuation of application No. 09/074,789, filed on May 8, 1998, now Pat. No. 6,071,915.
(60) Provisional application No. 60/046,236, filed on May 12, 1997.

(51) Int. Cl.$^7$ ............................................ C07D 295/14
(52) U.S. Cl. ...................... 544/393; 544/230; 544/360; 544/372; 544/373; 544/392
(58) Field of Search ................................ 544/392, 393

(56) References Cited

U.S. PATENT DOCUMENTS

| | | | |
|---|---|---|---|
| 4,069,336 A | 1/1978 | Lange et al. ................. 424/274 |
| 4,560,686 A | * 12/1985 | Nagano et al. ............. 514/255 |
| 4,841,051 A | 6/1989 | Shiozawa et al. ........... 544/287 |
| 5,380,725 A | 1/1995 | Abou-Gharbia et al. |
| 5,403,847 A | 4/1995 | Gluchowski et al. ....... 514/318 |
| 5,807,856 A | 9/1998 | Bock et al. |
| 6,063,785 A | * 5/2000 | Kuo et al. ................... 514/253 |
| 6,218,396 B1 | * 4/2001 | Kuo et al. ............. 514/253.01 |
| 6,362,338 B1 | * 3/2002 | Kuo et al. .................. 544/394 |

FOREIGN PATENT DOCUMENTS

| | | | |
|---|---|---|---|
| EP | 0711757 A | 11/1984 | |
| EP | 0558245 | 9/1993 | |
| GB | 2 201 676 | 9/1988 | |
| HU | 199858 | 3/1990 | |
| WO | WO 84/04302 | 11/1984 | .......... A61K/31/44 |
| WO | WO 94/00442 | 1/1994 | |
| WO | WO 95/04049 | 2/1995 | |

OTHER PUBLICATIONS

Bruno JF, Whittaker J, Song J. and Berelowitz M (1991) Molecular cloning and sequencing of a cDNA encoding a human α1A adrenergic receptor. Biochem. Biophys. Res. Commun. 179: 1485–1490.

Bylund DB, Eikenberg DC, Hieble JP, Langer SZ, Lefkowitz RJ, Minneman KP, Molinoff PB, Ruffolo RR, and Trendelenburg U (1994) IV. International Union of Pharmacology nomenclature of adrenoceptors. Pharmacol. Rev. 46: 121–136.

Carruthers SG (1994) Adverse effects of a α1–adrenergic blocking drugs. Drugs Safety 11: 12–20.

Faure c, Gouhier C, Langer SZ, and Graham D (1995) Quantification of α1–adrenoceptor subtypes in human tissues by competitive RT–PCR analysis. Biochem Biophys. Res. Commun. 213: 935–943.

Flavahan NA and VanHoutte PM (1986) α1–Adrenoceptor subclassification in vascular smooth muscle. Trends Pharmacol. Sci. 7: 347–349.

Ford APDW, Arredondo NF, Blue DR, Bonhaus DW, Jasper, J, Kava MS, Lesnick J, Pfister JR, Shieh IA, Vimont RL, Williams TJ, McNeal JE, Stamey TA, and Clarke DE (1996) RS–17053 (N–[2–(2–Cyclopropylmethoxyphenoxy)ethyl]–5–chloro–a, a–dimethyl–1H–indole–3–ethanamine hydrochloride), a selective α1A–adrenoceptor antagonist, displays low affinity for functional α1–adrenoceptors in human prostate: Implications for adrenoceptor classification. Mol. Pharmacol. 49: 209–215.

Forray C, Bard JA, Wegzel JM, Chiu G, Shapiro E, Tang R, Lepor H, Hartig PR, Weinshank RL, Branchek TA, and Gluchowski C (1994) The α1–adrenergic receptor that mediates smooth muscle contraction in human prostate has the pharmacological properties of the cloned human α1c subtype. Mol. Pharmacol. 45: 703–708.

Gormley G, Stoner E, Bruskewitz RC et al. (1992) The effect of finasteride in men with benign prostatic hyperplasia. N. Engl. J. Med. 327: 1185–1191.

Harrison JK, Pearson WR, and Lynch KR (1991) Molecular characterization of α1– and α2– adrenoceptors. Trends Pharmacol. Sch. 12: 62–67.

(List continued on next page.)

Primary Examiner—Emily Bernhardt
(74) Attorney, Agent, or Firm—Ruby T. Hope

(57) ABSTRACT

This invention relates to a series of arylsubstituted piperazines, of Formula I

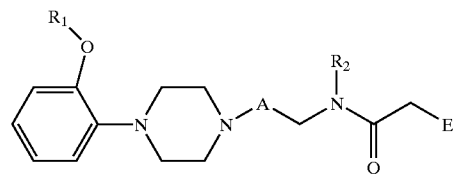

pharmaceutical compositions containing them and intermediates used in their manufacture. The compounds of the invention selectively inhibit binding to the α-1a adrenergic receptor, a receptor which has been implicated in benign prostatic hyperplasia. As such the compounds are potentially useful in the treatment of this and other disease.

3 Claims, 1 Drawing Sheet

OTHER PUBLICATIONS

Hieble JP and Caine M (1986) Etiology of benign prostatic hyperplasia and approaches to pharmacological management. Fed. Proc. 45: 2601–2603.

Hirasawa A, Horie K, Tanaka T, Takagaki K, Murai M, Yano J., and Tsujimoto G (1993) Cloning, functional expression and tissue distribution of human cDNA for the α1c–adrenergic receptor. Biochem. Biophys. Res. Commun. 195: 902–909.

Holck MI, Jones CHM, and Haeusler G (1983) Differential interactions of clonidine and methoxamine with postsynaptic α–adrenoceptors of rabbit main pulmonary artery. J Cardiovasc. Pharm. 5: 240–248.

Lepor H and Rigaud G (1990) The efficacy of transurethral resection of the prostate in men with moderate symptoms of prostatism. J. Urol. 143: 533–537.

Lepor H (1995) α–Blockade for benign prostatic hyperplasia (BPH) J Clin. Endocrinol. Metab. 80:750–753.

Marshall I, Burt RP, Andersson PO, Chapple CR, Greengrass PM, Johnson GI, and Wyllie MC (1992) Human α1c–adrenoceptor: functional characterisation in prostate. Br. J. Pharmacol. 107 (Proc. Suppl. Dec.): 327P.

Marshall I, Burt RP, and Chapple CR (1995) Noradrenaline contractions of human prostate mediated by α1A–(α1c–) adrenoceptor subtype. Br. J. Pharmacol. 115:781–786.

Mebust WK, Holtgrewe HL, Cockett ATK<and Peters PC (1989) Transurethral prostatectomy: immediate and postoperative complication: a cooperative study of 13 participating institutions evaluating 3,885 patients J. Urol. 141: 243–257.

Minneman KP, Han C and Abel PW (1988) Comparison of α1–adrenergic receptor subtypes distinguished by chloroethylclonidine and WB4101. Mol. Pharmacol. 33: 509–514.

Minneman KP and Esbenshade TA (1994) α1–Adrenergic receptor subtypes. Annu. Rev. Pharmacol. Toxicol. 34: 117–133.

Morrow AL and Creese I (1986) Characterization of α1–adrenergic receptor subtypes in rat brain: A reevaluation of [3H]WB4104 and [3H]prazosin binding. Mol. Pharmacol. 29: 321–330.

Muramatsu I (1992) A pharmacological perspective of α1–adrenoceptors: subclassification and functional aspects, in α1–Adrenoceptors (Fujiwara M, Sugimoto T, and Kogure K, eds.). Excerpta Medica Ltd., Tokyo, 193–202.

Muramatsu I, Oshita M, Ohmura T, Kigoshi S, Akino H, Gobara M, and Okada K (1994) Pharmacological characterization of α1–adrenoceptor subtypes in the human prostate: functional and binding studies. Br., J. Urol. 74: 572–577.

Oesterling JE (1995) Benign prostatic hyperplasia. Medical and minimally invasive treatment options. N. Engl. J. Med. 332: 99–109.

Price DT, Lefkowitz RJ, Caron MG, Berkowitz D, and Schwinn DA (1994) Localization of mRNA for three distinctα1–adrenergic receptor subtypes in human tissues: implications for human α–adrenergic physiology. Mol. Pharmacol. 45: 171–175.

Ramarao CS, Kincade Denker JM, Perez DM, Gaivin RJ, Riek RP, and Graham RM (1992) Genomic organization and expression of the human α1B–adrenergic receptor. J. Biol. Chem. 267: 21936–21945.

Schwinn DA, Johnston GI, Page SO, Mosley MJ, Wilson KH, Worman NP, Campbell S, Fidock MD, Furness LM, Parry–Smith DJ, Peter B, and Bailey DS (1995) Cloning and pharmacological characterization of human alpha–1 adrenergic receptors: sequence corrections and direct comparison with other species homologues. JPET 272: 134–142.

Weinberg DH, Trivedi P, Tan CP, Mitra S, Perkins–Barrow A, Borkowski D, Strader CD, and Bayne M (1994) Cloning, expression and characterization of human α adrenergic receotors α1A, α1B, and α1C. Biochem. Biophys. Res. Commun. 201: 1296–1304.

Weis KA, Epstein RS, Huse DM, Deverka PA and Oster G (1993) The costs of prostatectomy for benign prostatic hyperplasia. Prostate 22: 325–334.

Wennberg JE, Roos N, Sola L, Schori A, and Jaffe R (1987) Use of claims data systems to evaluate health care outcomes: mortality and reoperation following prostatectomy. JAMA 257: 933–936.

Yamada S, Tanaka C, Kimura R, and Kawabe K (1994) Alpha 1–adrenoceptors in human prostate: characterization and binding characteristics of alpha 1–antagonists. Life Sci. 54: 1845–1854.

Barry M, Roehrborn C (1994) Management of Benign Prostatic Hyperplasia. Annual Review. 4*: 177–188.

Steers W, Zorn B (1995) Benign Prostatic Hyperplasia, Disease–a–Month, vol. XLI No. 7 440–497.

Raghupathi RK et al., (1991) Analogues of the 5HT–1A–serotonin antagonist 1–(2–methoxyphenyl)–4–'4–(2–phthalimido)butyl!piperazine with reduced alpha–1–andrenergic affinity. Jour. Med. Chem., vol 34, No. 8, pp. 2633–2638, XP0020074047.

Orjales A, et al., (1995) New (2–methoxyphenyl) piperazine derivatives as 5–HT–1A receptor ligands with reduced alpha–1–adrenergic activity. Synthesis and structure–affinity relationships. Journ. Med. Chem., vol. 38, No. 8, pp. 1273–1277, XP002074046.

Breslin D, Fields DW, Chou TC, Marion DN, Kane M, Vaughan ED, and Felsen D (1993) Medical management of benign prostatic hyperplasia: a canine model comparing the in vivo efficacy of alpha–1 adrenergic antagonists in the prostate. J. Urol. 149:395–399.

Hatano A., Takahashi H, Tamaki M, Komeyama T, Koizumi T, and Takeda M (1994) Pharmacological evidence of a distinct α1–adrenoceptor subtypes mediating the contraction of human prostatic urethra and peripheral artery. Br. J. Pharmacol. 113:723–728.

Lepor H, Auerbach S, Puras–Baez A et al. (1992) A randomized, placebo–controlled multicenter study of the efficacy and safety of terazosin in the treatment of benign prostatic hyperlasia. J. Urol. 148:1467–1474.

Hungarian Novelty Search Report, dated Nov. 6, 2002, for Hungarian Appln. No. P0100048.

* cited by examiner

Effects of Compound 5 upon IUP and MAP at 10 μg/kg PE in dogs

Effects of Compound 12 upon IUP and MAP at 10 μg/kg PE in dogs

ARYLSUBSTITUTED PIPERAZINES USEFUL IN THE TREATMENT OF BENIGN PROSTATIC HYPERPLASIA

This application is a divisional application of U.S. Ser. No. 09/526,224, filed Mar. 15, 2000 now U.S. Pat. No. 6,303,594 which is a continuation of U.S. Ser. No. 09/074,789, filed May 8, 1998 now U.S. Pat. No. 6,071,915; which claims priority from U.S. Provisional Application Ser. No. 60/046,236, filed May 12, 1997.

This invention relates to a series of arylsubstituted piperazines, pharmaceutical compositions containing them and intermediates used in their manufacture. The compounds of the invention selectively inhibit binding to the $\alpha\text{-}1_a$ adrenergic receptor, a receptor which has been implicated in benign prostatic hyperplasia. In addition, compounds of the invention reduce intraurethral pressure in an in vivo model. As such the compounds are useful in the treatment of this disease.

BACKGROUND

Benign prostatic hyperplasia (BPH), a nonmalignant enlargement of the prostate, is the most common benign tumor in men. Approximately 50% of all men older than 65 years have some degree of BPH and a third of these men have clinical symptoms consistent with bladder outlet obstruction (Hieble and Caine, 1986). In the U.S., benign and malignant diseases of the prostate are responsible for more surgery than diseases of any other organ in men over the age of fifty.

There are two components of BPH, a static and a dynamic component. The static component is due to enlargement of the prostate gland, which may result in compression of the urethra and obstruction to the flow of urine from the bladder. The dynamic component is due to increased smooth muscle tone of the bladder neck and the prostate itself (which interferes with emptying of the bladder) and is regulated by alpha 1 adrenergic receptors ($\alpha$1-ARs). The medical treatments available for BPH address these components to varying degrees, and the therapeutic choices are expanding.

Surgical treatment options address the static component of BPH and include transurethral resection of the prostate (TURP), transurethral incision of the prostate (TUIP), open prostatectomy, balloon dilatation, hyperthermia, stents and laser ablation. TURP is the preferred treatment for patients with BPH and approximately 320,000 TURPs were performed in the U.S. in 1990 at an estimated cost of $2.2 billion (Weis et al., 1993). Although an effective treatment for most men with symptomatic BPH, approximately 20–25% of patients do not have a satisfactory long-term outcome (Lepor and Rigaud, 1990). Complications include retrograde ejaculation (70–75% of patients), impotence (5–10%), postoperative urinary tract infection (5–10%), and some degree of urinary incontinence (2–4%) (Mebust et al., 1989). Furthermore, the rate of reoperation is approximately 15–20% in men evaluated for 10 years or longer (Wennberg et al., 1987).

Apart from surgical approaches, there are some drug therapies which address the static component of this condition. Finasteride (Proscar®, Merck), is one such therapy which is indicated for the treatment of symptomatic BPH. This drug is a competitive inhibitor of the enzyme 5a-reductase which is responsible for the conversion of testosterone to dihydrotestosterone in the prostate gland (Gormley et al., 1992). Dihydrotestosterone appears to be the major mitogen for prostate growth, and agents which inhibit 5a-reductase reduce the size of the prostate and improve urine flow through the prostatic urethra. Although finasteride is a potent 5a-reductase inhibitor and causes a marked decrease in serum and tissue concentrations of dihydrotestosterone, it is only moderately effective in treating symptomatic BPH (Oesterling, 1995). The effects of finasteride take 6–12 months to become evident and for many men the clinical improvement is minimal (Barry, 1997).

The dynamic component of BPH has been addressed by the use of adrenergic receptor blocking agents ($\alpha$1-AR blockers) which act by decreasing the smooth muscle tone within the prostate gland itself. A variety of $\alpha$1-AR blockers (terazosin, prazosin, and doxazosin) have been investigated for the treatment of symptomatic bladder outlet obstruction due to BPH, with terazosin (Hytrin, Abbott) being the most extensively studied. Although the $\alpha$1-AR blockers are well-tolerated, approximately 10–15% of patients develop a clinically adverse event (Lepor, 1995). The undesirable effects of all members of this class are similar, with postural hypotension being the most commonly experienced side effect (Lepor et al., 1992). In comparison to the 5a-reductase inhibitors, the a1-AR blocking agents have a more rapid onset of action (Steers, 1995). However, their therapeutic effect, as measured by improvement in the symptom score and the peak urinary flow rate, is moderate. (Oesterling, 1995)

The use of $\alpha$1-AR antagonists in the treatment of BPH is related to their ability to decrease the tone of prostatic smooth muscle, leading to relief of the obstructive symptoms. Adrenergic receptors are found throughout the body play a dominant role in the control of blood pressure, nasal congestion, prostrate function and other processes (Harrison et al., 1991). However, there are a number of cloned $\alpha$1-AR receptor subtypes: $\alpha 1_a$-AR, $\alpha 1_b$-AR and $\alpha 1_d$-AR (Bruno et al., 1991; Forray et al., 1994; Hirasawa et al., 1993; Ramarao et al., 1992; Schwinn et al., 1995; Weinberg et al., 1994). A number of labs have characterized the $\alpha$1-ARs in human prostate by functional, radioligand binding, and molecular biological techniques (Forray et al., 1994; Hatano et al., 1994; Marshall et al., 1992; Marshall et al., 1995; Yamada et al., 1994). These studies provide evidence in support of the concept that the $\alpha 1_a$-AR subtype comprises the majority of $\alpha$1-ARs in human prostatic smooth muscle and mediates contraction in this tissue. These findings suggest that the development of a subtype-selective $\alpha 1_1$-AR antagonist might result in a therapeutically effective agent with greater selectivity for the treatment of BPH.

SUMMARY OF THE INVENTION

The invention relates to compounds of Formula I

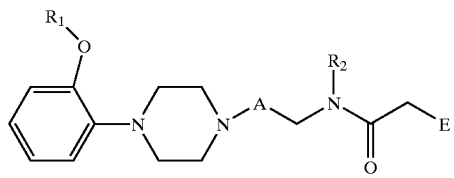

wherein:
  A is $(CH_2)_n$ where n is 1–6;
  $R_1$ is $C_{1-6}$alkyl, phenyl,
    substituted phenyl
      where the phenyl substituents are independently selected from one or more of the group consisting of $C_{1-5}$alkyl, $C_{1-5}$alkoxy and halogen, phenyl$C_{1-5}$alkyl, or
    substituted phenyl$C_{1-5}$alkyl where the phenyl substituents are independently selected from one or more of the group consisting of $C_{1-5}$alkyl, $C_{1-5}$alkoxy and halogen;

$R_2$ is hydrogen, $C_{1-6}$alkyl, $C_{1-5}$alkenyl, $C_{2-5}$ alkenyl, phenyl$C_{2-5}$alkynyl, or substituted phenyl$C_{1-5}$alkyl
where the phenyl substituents are independently selected from one or more of the group consisting of $C_{1-5}$alkyl, $C_{1-5}$alkoxy and halogen;

E is

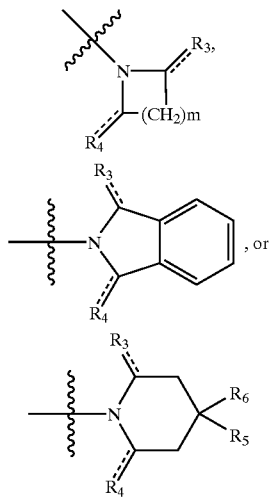

where:
m is 1–5;
$R_3$ is hydrogen, $C_{1-6}$alkyl or oxygen,
where if $R_3$ is oxygen, the hashed line represents a bond and if $R_3$ is $C_{1-6}$alkyl the hashed line is absent;
$R_4$ oxygen, hydrogen, $C_{1-5}$alkyl, formyl, carboxy, $C_{1-5}$alkylcarbonyl, $C_{1-5}$alkoxycarbonyl, phenyl$C_{1-5}$alkoxy, substituted phenyl$C_{1-5}$alkoxy
where the phenyl substituents are independently selected from one or more of the group consisting of $C_{1-5}$alkyl, $C_{1-5}$alkoxy and halogen, amide, and substituted amide
where the nitrogen substituents are independently selected from one or more of the group consisting or hydrogen, $C_{1-5}$alkyl, $C_{1-5}$alkoxy and hydroxy,
where if $R_4$ is oxygen, the dashed line represents a bond and if $R_4$ is any other substituent, the dashed line is absent;
$R_5$ is hydrogen, $C_{1-5}$alkyl or taken together with $R_6$ to form a cyclohexane, cyclopentane or cyclopropane ring;
$R_6$ is hydrogen, $C_{1-5}$alkyl or taken together with $R_5$ to form a cyclohexane, cyclopentane or cyclopropane ring;
and pharmaceutically acceptable salts thereof.

These compounds are useful as adrenergic receptor modulating agents. The compounds of this invention selectively bind to the $\alpha1_a$-AR receptor, modulate the activity of said receptor and are selective for prostate tissue over aortic tissue. As such, they represent a viable treatment for $\alpha1_a$-AR receptor modulated disorders which include but are not limited to BPH.

In addition this invention contemplates pharmaceutical compositions containing compounds of Formula I, and methods of treating disorders mediated by $\alpha1_a$-AR receptor with compounds of Formula I.

Aside from compounds of Formula I, this invention contemplates intermediate compounds of Formula II. These intermediates are useful in the preparation of compounds of Formula I and are as follows:

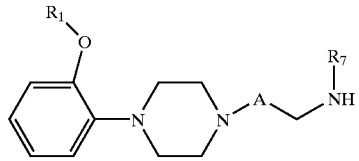

II wherein:
A is $(CH_2)_n$ where n is 1–6;
$R_1$ is $C_{2-6}$ alkyl, phenyl,
substituted phenyl
where the phenyl substituents are independently selected from one or more of the group consisting of $C_{1-5}$alkyl, $C_{1-5}$alkoxy and halogen, phenyl$C_{1-5}$alkyl, or
substituted phenyl$C_{1-5}$alkyl
where the phenyl substituents are independently selected from one or more of the group consisting of $C_{1-5}$alkyl, $C_{1-5}$alkoxy and halogen;
$R_7$ is hydrogen, BOC or CBZ.

Still further this invention contemplates compounds of Formula III. These compounds are useful as intermediates in the preparation of compounds of Formula I and are as follows.

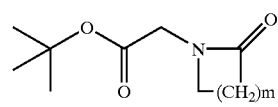

III wherein:
m is 1–5.

DETAILED DESCRIPTION OF THE INVENTION

Figure 1:
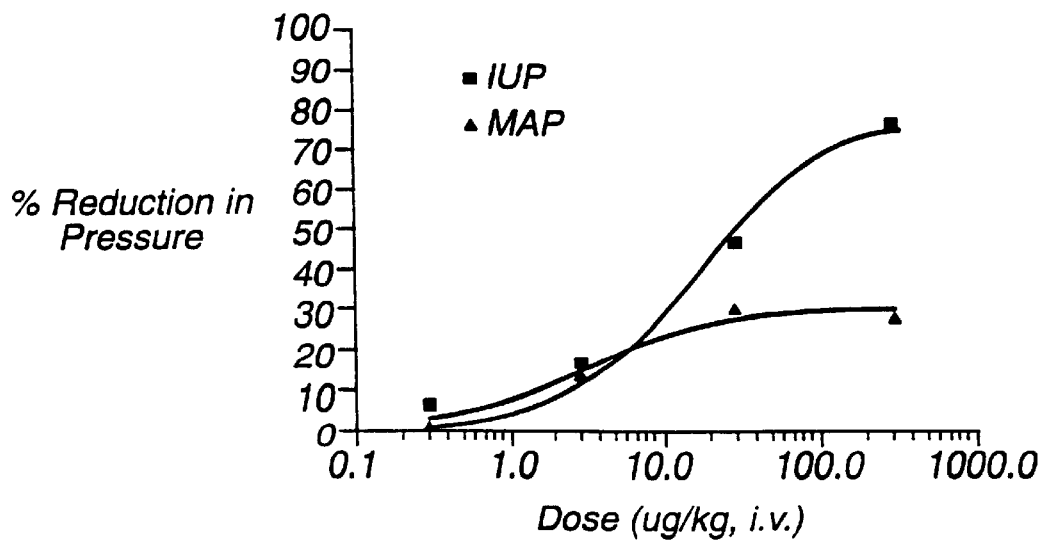
FIG. 1 illustrates the effect of compound 5 on IUP and MAP.

The terms used in describing the invention are commonly used and known to those skilled in the art. "HBSS" refers to Hank's Balanced Salt Solution. "Independently" means that when there are more than one substituent, the substitutents may be different. The term "alkyl" refers to straight, cyclic and branched-chain alkyl groups and "alkoxy" refers O-alkyl where alkyl is as known α1-AR antagonists, defined supra, "LDA" refers to lithium diiopropylamide, and "BOP" refers to bezotriazole-1-yl-oxy-tris-(dimethylamino)-phoxphoniumhexafluorophosphate. "BOC" refers to t-butoxycarbonyl, "PyBroP" refers to bromo-tris-pyrrolidino-phosphonium hexafluorophosphate, "CBZ" refers to benzyloxycarbonyl, and "Ts" refers to toluenesulfonyl. "DCC" refers to 1,3-dicyclohexylcarbodiimide, "DMAP" refers to 4-N'N-dimethylaminopyridine, "EDCI" refers to 1-(3-dimethylamionpropyl)-3-ethylcarbodiimide hydrochloride, and "HOBT" refers to 1-hydroxybenzotriazole hydrate. The symbol "Ph" refers to phenyl and "PHT" refers to phthalimido. The term "effective dose" refers to an amount of a compound of Formula I which binds to an/or antagonizes the activity of the $\alpha 1_a$ adrenergic receptor. In addition, the term "effective dose" refers to an amount of a compound of Formula I which reduces the symptoms of diseases associated with the $\alpha$-$1_a$ adrenergic receptor.

The compounds of the invention may be prepared by the following schemes, where some schemes produce more than one embodiment of the invention. In those cases, the choice of scheme is a matter of discretion which is within the capabilities of those of synthetic chemists.

Compounds of Formula I where $R_1$ is phenyl, $R_2$ is hydrogen, $R_3$ is oxygen, A is $(CH_2)_3$ and m is 4, may be prepared as illustrated by Scheme 1. In this scheme, the molecules of Formula I are prepared in a convergent synthesis where two halves of the molecule are assembled and ultimately coupled together.

The starting material for one half is a mono N-substituted piperazine of type 1a. Treatment of 1a with a mild base such as $K_2CO_3$ and an alkylating agent, such as acrylonitrile in an inert solvent such as MeOH at room temperature for 2–24 hours gives the nitrile 1b. This intermediate may be hydrogenated using Rainy Nickel as a catalyst to give the propylamine intermediate 1c. The other half of the molecule is assembled using compounds of type 1c as starting materials. $\epsilon$-Caprolactam is treated with a strong base such as NaH, in an inert solvent at 0° C. for about 30 minutes. The formed anion is treated with an alkylating agent such as t-butylbromoacetate in an inert solvent such as acetonitrile at room temperature for two hours to 2 days to give the ester 1e. Hydrolysis of 1e with an acid such as trifluoroacetic acid at room temperature over 2–16 hours gives the acid 1f. Treatment of the amine 1c and the acid 1f with a peptide coupling agent such as BOP and a suitable amine such as DMAP at room temperature over 1–16 hours gives a compound of Formula I, 1g. Other coupling agents may be substituted for BOP. Such agents include but are not limited to, PyBroP, EDCI, HOBt and the like. Suitable DMAP replacements include but are not limited to N-methylmorpholine, imidazole, DABCO and the like.

Scheme 1 may be used to prepare compounds aside from 1g. To prepare compounds where m is 1–5, known lactams of the appropriate ring size such as 2-azacyclooctanone, replace $\epsilon$-caprolactam in Scheme 1.

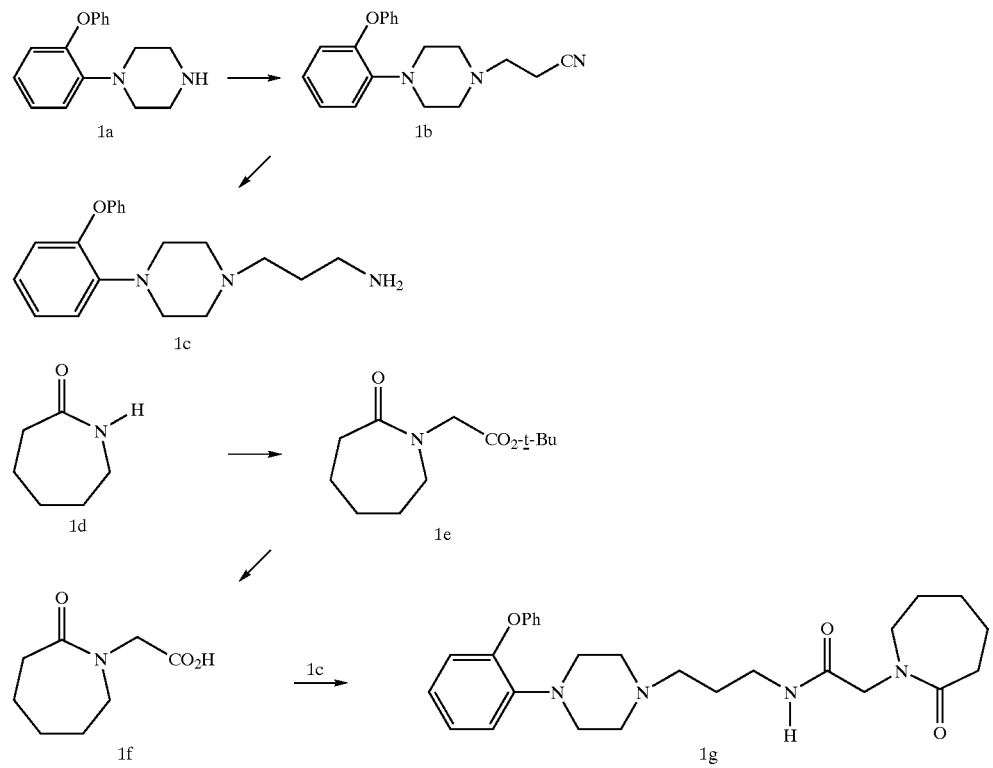

Scheme 1

To prepare compounds where $R_1$ is other than phenoxy, 1a is replaced with known phenyl piperazine derivatives such as N-(2-t-butoxyphenyl)-piperazine. To prepare compounds where A is $(CH_2)_n$ and n is 1–6, acrylonitrile may be replaced with alkylating agents such as 4-chlorobutyronitrile. Alternatively, intermediate 1c may be prepared by another route as illustrated in Scheme 2.

Piperazine derivative 1a is treated with a mild base and known phthalimido derivatives such as N-(4-bromobutyl) phthalimide to give intermediate 2a. Treatment of 2a with a hydrazine such as N-methyl hydrazine in a suitable solvent such as MeOH or EtOH at reflux, gives intermediates of type 1c. Alternatively, piperazine 1a is treated with a mild base and an N-BOC protected amine such as N-tert-butoxycarbonyl4-bromobutylamine to give the corresponding BOC protected amine. This amine can be deprotected by treatment with an acid such as TFA to give intermediates of type 1c.

Scheme 2

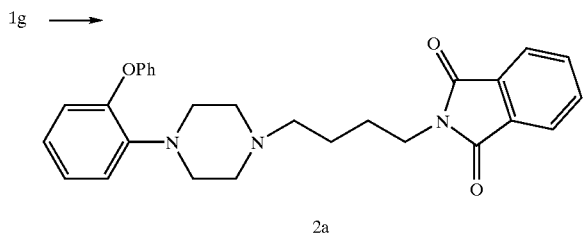

To prepare compounds where R₂ is other than hydrogen, Scheme 3 may be used. Treatment of compounds of type 1g with a strong base such as NaH, followed by an alkylating agent such as benzyl bromide gives compounds of type 3a in 1–5 hours at temperatures from about 0–35° C.

Scheme 3

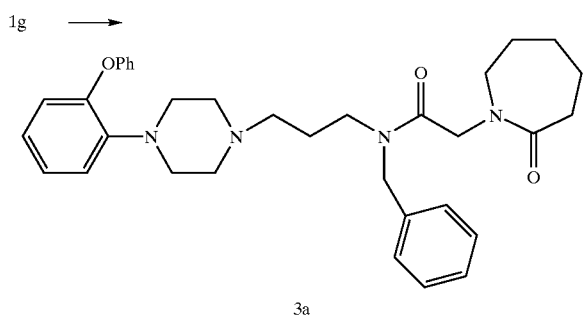

Compounds where $R_4$ is oxygen, $C_5$alkyl, formyl, carboxy, $C_{1-5}$alkylcarbonyl, $C_{1-5}$alkoxycarbonyl, phenyl$C_{1-5}$alkoxy, substituted phenyl$C_{1-5}$alkoxy, amide and substituted amide may be synthesized by Scheme 4. For example to prepare compounds where $R_4$ is ethoxycarbonyl, m is 2, and $R_3$ is carbonyl, treat ethyl-2-pyrrolidone-5-carboxylate with a strong base such as NaH, in an inert solvent at 0° C. for about 30 minutes. The formed anion is treated with an alkylating agent such as t-butylbromoacetate in an inert solvent such as acetonitrile at room temperature for two hours to 2 days to give the ester 4a. Acidic hydrolysis of 4a with trifluoroacetic acid at room temperature over 2–16 hours gives the acid 4b. Coupling of the acid 4b and the intermediate amine 1c with a peptide coupling agent such as PryBOP gives a compound of Formula I, 4c. The ethyl ester of compound 4c may be treated with a variety of agents to give derivatives such as amides, carboxylic acids, aldehydes etc, where the reagents and reaction conditions are within the knowledge of those skilled in the art.

Scheme 4

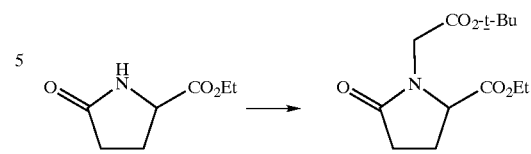

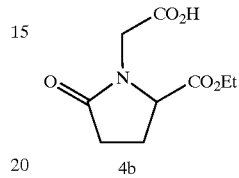

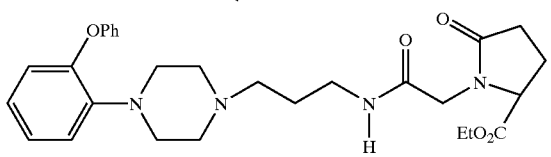

Although the claimed compounds are useful as modulators of α1-AR, some compounds are either preferred or particularly preferred. The preferred compounds of the invention include:

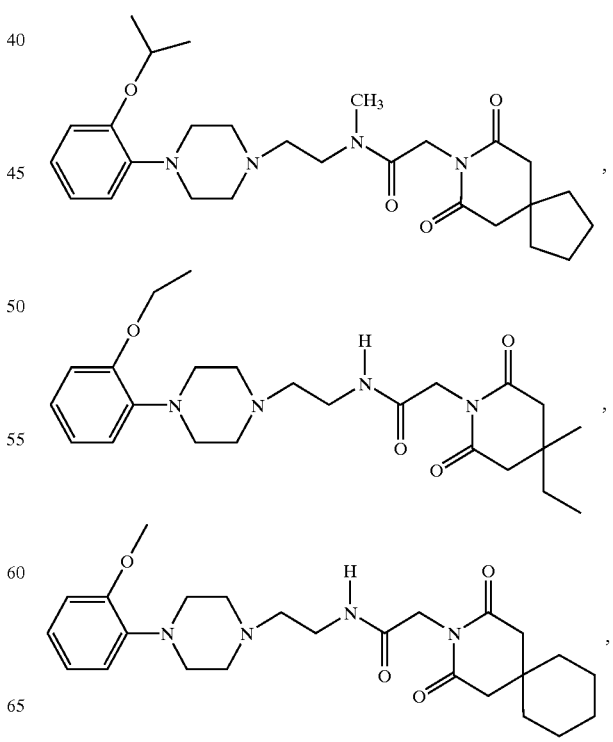

-continued

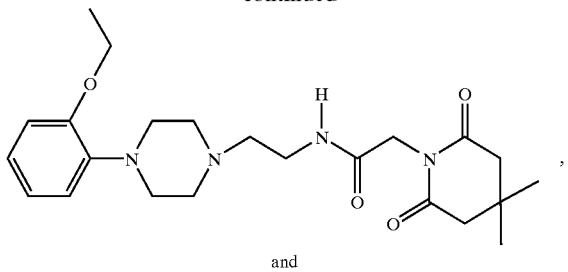

and

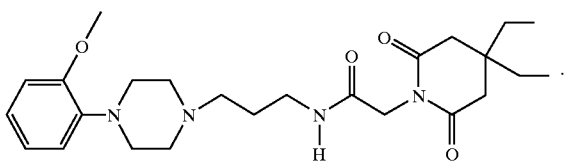

The particularly preferred "$R_1$"s are $C_{1-5}$alkyl.

The particularly preferred "$R_2$"s are hydrogen, $C_{2-5}$alkenyl and $C_{2-5}$alkynyl.

The particularly preferred "E"s are

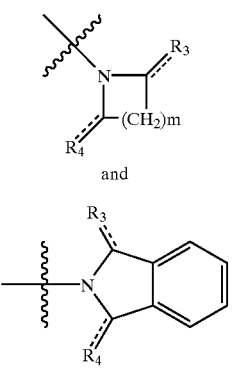

and

The particularly preferred "m" is 3.

The particularly preferred $R_3$ is oxygen.

The particularly preferred $R_4$ is hydrogen.

The particularly preferred "A"s are $(CH_2)_n$ where n is 2–4.

The particularly preferred compounds of Formula II include compounds where A is 2 or 3, $R_1$ is $C_{2-6}$alkyl, and $R_7$ is hydrogen.

The particularly preferred compounds of Formula III include compounds where m is 3.

The compounds of Formula I may be used in pharmaceutical compositions to treat patients with disorders related to modulating the activity of the α1 adrenergic receptor. The preferred route is oral administration, however compounds of the invention may be administered by other methods, including but not limited to intravenous infusion. Oral doses range from about 0.01–100 mg/kg daily. The preferred oral dosage range is from about 0.05–1.0 mg/kg daily. Infusion doses can range from about 0.001–100 mg/kg/min of inhibitor, with a pharmaceutical carrier over a period ranging from several minutes to several days.

The pharmaceutical compositions can be prepared using conventional pharmaceutical excipients and compounding techniques. Oral dosage forms may be elixers, syrups, capsules tablets and the like. Where the typical solid carrier is an inert substance such as lactose, starch, glucose, methyl cellulose, magnesium sterate, dicalcium phosphate, mannitol and the like; and typical liquid oral excipients include ethanol, glycerol, water and the like. All excipients may be mixed as needed with disintegrants, diluents, granulating agents, lubricants, binders and the like using conventional techniques known to those skilled in the art of preparing dosage forms. Parenteral dosage forms may be prepared using pharmaceutically acceptable carriers or diluents, including but not limited to water or another sterile carrier.

Typically the compounds of Formula I are isolated and used as free bases, however the compounds may be isolated and used as their pharmaceutically acceptable salts. Examples of such salts include but are not limited to hydrobromic, hydroiodic, hydrochloric, perchloric, sulfuric, maleic, fumaric, malic, tartatic, citric, benzoic, mandelic, methanesulfonic, hydroethanesulfonic, benzenesulfonic, oxalic, pamoic, 2-naphthalenesulfonic, p-toluenesulfonic, cyclohexanesulfamic and saccharinic.

In order to illustrate the invention the following examples are included. These examples do not limit the invention. They are meant only to suggest a method of practicing the invention. Those skilled in the art may find other methods of practicing the invention, which will be readily apparent to them. However those methods are deemed to be within the scope of this invention.

PREPARATIVE EXAMPLES

Example 1

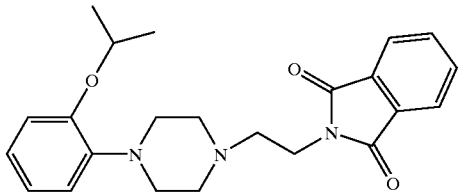

Cpd. 1

1-(2-phthalimidoethyl)-4-(2-isopropyloxyphenyl)piperazine

N-(2-Bromoethyl)phthalimide (7.6 g, 30 mmol) and $K_2CO_3$ (6.2 g, 45 mmol) were added to a solution of N-1-(2-isopropoxyphenyl)piperazine (6.6 g, 30 mmol) in acetonitrile (100 mL) and the resulting mixture was heated at reflux for 2 days. The mixture was concentrated in vacuo and purified by column chromatography on silica gel using EtOAc/hexanes (30:70) as an eluent gave the title compound as a solid: MS m/z 394 (MH$^+$).

Example 2

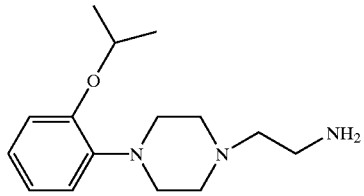

Cpd. 2

1-(2-Aminoethyl)-4-(2-2-<u>iso</u>-propyloxyphenyl)piperazine

A solution of compound 1 (7.5 g, 19 mmol) in EtOH (70 mL) was stirred for 10 minutes at room temperature. Methylhydrazine (20 mL) was added and the mixture was heated at reflux for 2.5 hours. The mixture was cooled to room temperature and the resulting solid precipitate was removed by filtration. The filtrate was concentrated in vacuo yielded the title compound as solid which was used without purification: MS m/z 264 (MH$^+$).

Example 3

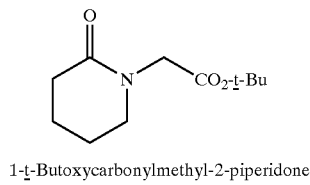

1-t-Butoxycarbonylmethyl-2-piperidone

Cpd. 3

95% Sodium Hydride (1.67 g, 66 mmol) was added to a stirred solution of δ-valerolactam (5.95 g, 60 mmol) in toluene (100 mL) at 0° C. and the resulting suspension was stirred for 1 hours. t-Butylbromoacetate (8.86 mL, 60 mmol) was added dropwise and the reaction mixture was warmed to room temperature and stirred for 10 hours. Saturated NH$_4$Cl aq was added and the resulting organic layer was washed with successive portions of brine and H$_2$O. The combined organic layers were dried (Na$_2$SO$_4$) and concentrated in vacuo to give compound 3 as an oil.

Example 4

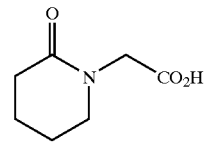

1-Carbonymethyl-2-piperdone

Cpd. 4

Trifluoroacetic acid (15 mL) was added to a stirred solution of compound 2 (12.93 g, 61 mmol) in methylene chloride (30 mL) under N$_2$. This mixture was stirred for 4 hours and concentrated in vacuo to give the title compound as a solid: MS m/z 158 (MH$^+$).

Example 5

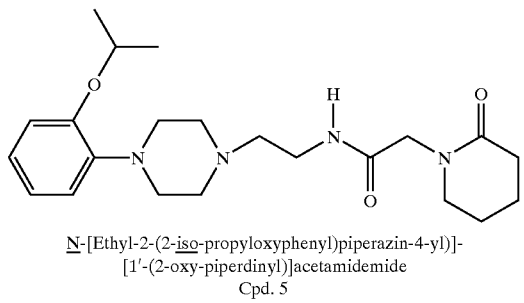

N-[Ethyl-2-(2-iso-propyloxyphenyl)piperazin-4-yl)]-
[1'-(2-oxy-piperdinyl)]acetamidemide
Cpd. 5

A solution of compound 2 (3.61 g, 23 mmol) in methylene chloride (10 mL) was added to a solution of compound 4 (5.0 g, 19 mmol) in methylene chloride (10 mL). PyBroP (10.72 g, 23 mmol), DMAP (3.85 g, 31 mmol) and N-methylmorpholine (2.53 mL, 23 mmol) were added and the mixture was stirred at room temperature under N$_2$ for 10 hours. The resulting mixture was washed with one portion of aqueous sodium bicarbonate, brine and H$_2$O. The combined organic layer was dried (Na$_2$SO$_4$) and concentrated in vacuo. The residue was purified by MPLC on silica gel using EtOAc/MeOH/triethylamine (90:5:5) as an eluent to give the title compound as an oil: MS m/z 403 (MH$^+$). Treatment of the isolated compound with an equimolar portion of citric acid in ethyl acetate gave the citrate salt of the title compound as a solid.

Example 6

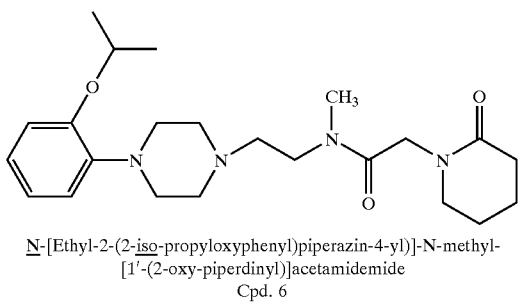

N-[Ethyl-2-(2-iso-propyloxyphenyl)piperazin-4-yl)]-N-methyl-
[1'-(2-oxy-piperdinyl)]acetamidemide
Cpd. 6

Sodium hydride (95% tech. 10.6 mg, 0.44 mmol) was added to a stirred solution of compound 5 (140.5 mg, 0.35 mmol) in THF (5 mL) at 0° C. and the resulting suspension was stirred for 30 minutes. Methyl iodide (0.37 mmol) was added dropwise and the mixture was stirred overnight at room temperature. The residue was concentrated in vacuo, dissolved in ethyl acetate and washed with successive portions of aqueous, sat. ammonium chloride solution, brine and water. The combined organic layer was dried (Na$_2$SO$_4$) and concentrated in vacuo to give the title compound as a solid: MS m/z 417 (MH$^+$).

BIOLOGICAL EXAMPLES

Biological activity and selectivity of compounds of the invention was demonstrated by the following in vitro assays. The first assay tested the ability of compounds of Formula I to bind to membrane bound receptors α1$_a$-AR, α1$_b$-AR and α1$_d$-AR.

Example 14

The DNA sequences of the three cloned human α1-AR subtypes have been published. Furthermore, the cloned cDNAs have been expressed both transiently in COS cells and stably in a variety of mammalian cell lines (HeLa, LM(tk-), CHO, rat-1 fibroblast) and have been shown to retain radioligand binding activity and the ability to couple to phosphoinositide hydrolysis. We used published DNA sequence information to design primers for use in RT-PCR amplification of each subtype to obtain cloned cDNAs. Human poly A+ RNA was obtained from commercially available sources and included hippocampus and prostate samples, sources which have been cited in the literature. For the primary screen a radio ligand binding assay was used which employed membrane preparations from cells expressing the individual cloned receptor cDNAs. Radiolabeled ligands with binding activity on all three subtypes (non-selective) are commercially available ([125I]-HEAT, [3H]-prazosin).

Each α1 receptor subtype was cloned from poly A+ RNA by the standard method of reverse transcription-polymerase chain reaction (RT-PCR). The following sources of polyA+ RNA were used for the cloning of the α1 receptor subtypes: α1$_a$-AR, human hippocampus and prostate, α1$_b$-AR, human hippocampus, α1$_d$-AR, human hippocampus. The resulting cDNAs were cloned into the pcDNA3 mammalian expression vector (Invitrogen Corp., San Diego Calif.). Each DNA was sequenced for verification and to detect any possible mutations introduced during the amplification process. Any deviation in sequence from the published consensus for each receptor subtype was corrected by site-directed mutagenesis.

The three α1-AR subtypes (a, b, d) were transfected into COS cells using a standard DEAE-dextran procedure with a chloroquine shock. In this procedure, each tissue culture dish (100 mm) was inoculated with 3.5×10⁶ cells and transfected with 10 μg of DNA. Approximately 72 hours post-transfection, the cells were harvested and COS membranes were prepared. Transfected COS cells from 25 plates (100 mm) were scraped and suspended in 15 mL of TE buffer (50 mM Tris-HCl, 5 mM EDTA, pH7.4). The suspension was disrupted with a homogenizer. It was then centrifuged at 100×g for 10 minutes at 4° C. The supernatant was centrifuged at 34,500×g for 20 minutes at 4° C. The pellet was resuspended in 5 mL TNE buffer (50 mM Tris-HCl, 5 mM EDTA, 150 mM NaCl, pH7.4). The resulting membrane preparation was aliquoted and stored at −70° C. The protein concentration was determined following membrane solubilization with TritonX-100.

The ability of each compound to bind to each of the α1-AR subtypes was assessed in a receptor binding assay. [125I]-HEAT, a non-selective α1-AR ligand, was used as the radiolabeled ligand. Each well of a 96-well plate received: 140 μL TNE, 25 μL [125I]-HEAT diluted in TNE (50,000 cpm; final concentration 50 pM), 10 μL test compound diluted in DMSO (final concentration 1 pM-10 μM), 25 mL COS cell membrane preparation expressing one of the three α1 -AR subtypes (0.05–0.2 mg membrane protein). The plate was incubated for 1 hour at room temperature and the reaction mixtures were filtered through a Packard GF/C Unifilter filter plate. The filter plate was dried for 1 hour in a vacuum oven. Scintillation fluid (25 mL) was added to each well, and the filter plate was counted in a Packard Topcount scintillation counter. Data was analyzed using GraphPad Prism software.

Tables A & B list the IC$_{50}$ values expressed in nanomolar concentration for select compounds of the invention in all receptor subtypes.

TABLE A

| Cpd. | R$_1$ | A | R$_2$ | R$_4$ | m | α1a-AR | α1b-AR | α1d-AR |
|---|---|---|---|---|---|---|---|---|
| 5* | i-prop | CH$_2$ | H | H | 3 | 8.7 | 46120 | 372 |
| 6 | i-prop | CH$_2$ | CH$_3$ | H | 3 | 53 | 763900 | 650 |
| 7 | i-prop | CH$_2$ | CH$_2$CHCH$_2$ | H | 3 | 103 | 172500 | 372 |
| 8 | i-prop | CH$_2$ | CH$_2$(C)CH$_3$ | H | 3 | 237 | 170200 | 358 |
| 9 | i-prop | CH$_2$ | CH$_2$Ph | H | 3 | 88 | 4226 | 348 |
| 10 | i-prop | CH$_2$ | H | CO$_2$C$_2$H$_5$ | 2 | 20 | 26310 | 260 |
| 11 | i-prop | CH$_2$ | H | H | 4 | 18 | 3536 | 505 |
| 12 | CH$_3$ | (CH$_2$)$_2$ | H | H | 3 | 98 | 109000 | 30530 |

*indicates a citrate salt

TABLE B

| Cpd. | R$_1$ | A | R$_2$ | m | α1a-AR | α1b-AR | α1d-AR |
|---|---|---|---|---|---|---|---|
| 13 | i-prop | CH$_2$ | H | 3 | 18 | 1932 | 189 |

Example 15

The antagonist activity of select compounds of Formula I was demonstrated by the following screen. Binding of an agonist to α1-ARs causes the activation of PLC through G-protein coupled mechanisms (Minneman and Esbenshade, 1994). PLC catalyzes the hydrolysis of phosphatidyl inositol 4,5-bisphosphate (PIP2) generating two second messenger molecules, inositol 1,4,5-triphosphate (IP3) and diacylglycerol (DAG) and ultimately resulting in mobilization of intracellular calcium stores. Hits from the primary screening assay that showed selectivity in inhibiting radioligand binding to the α1$_a$-AR were evaluated for the ability to antagonize the mobilization of cytosolic calcium in cell lines stably expressing individual receptor subtypes.

Preparation of stable cell lines expressing each receptor subtype: The alpha 1 adrenergic receptor subtypes (a, b, d) in the pcDNA3 vector were transfected into HEK 293s (human embryonic kidney) cells to form stable receptor-expressing cell lines. Transfection was performed using DMRIE-C (GibcoBRL) cationic lipid reagent mixed with 2–3 ug of DNA and reduced serum OPTI-MEM 1 medium (GibcoBRL). Cells in 100 mm tissue culture plates were overlayed with the lipid-DNA complex and incubated at 37°

C., 5% $CO_2$ for 5–6 hours. Serum-containing growth medium was then added and cells were incubated for an additional 48 hours. Following this incubation, each plate was split 1:5 into selection medium containing 250, 300 or 350 ug/ml of G418 (geneticin) antibiotic. Plates were fed every 4 days with the appropriate selection medium. After approximately 3 weeks, colonies were picked for each subtype from the 300 ug/ml G418 selection plates. Colonies were expanded and frozen. Twelve cell lines of each subtype were screened for alpha 1 adrenergic receptor binding using a whole cell receptor binding assay. Positive cultures were subsequently analyzed by the calcium mobilization assay.

HEK 293s cells expressing human α1-AR were lifted with trypsin and washed once with HBSS. The cell pellet was resuspended in HBSS with 0.05% BSA to $1-5 \times 10^6$ cells/ml. A 5 mM Fluo-3 solution (in 2/13 vol. DMSO and 1/3 vol Pluronic acid) was added to the cell suspension, giving a final Fluo-3 concentration of 5 $\mu$M. Cells were then incubated with gentle rocking at room temperature for 1 hr in the dark. After incubation, the cells were washed 3× with HBSS and resuspended in HBSS with 1.25 mM $CaCl_2$ to $0.7 \times 10^6$ cell/ml. Cell aliquots (100 $\mu$l) were pippetted into each well of a 96-well microplate. Calcium mobilization was induced with norepinephrine (10 uM) at room temperature. Two minutes prior to assay, antagonists were added to cells utilizing a 96-well pipettor. Afterward, the agonist was added and fluorescent signal was monitored for 2–3 minutes using FLIPR (Molecular Devices, USA). Compound 5 inhibited the mobilization of cytosolic calcium at an $IC_{50}$ of 99 $\mu$M.

Example 16

The antagonist activity and the selectivity of compounds of the invention for prostate tissues over aortic tissues as well as their antagonists was demonstrated as follows. The contractile responses of rat prostatic tissue and rat aorta tissues were examined in the presence and absence of antagonist compounds. As an indication of the selectivity of antagonism, test compound effects on vascular smooth muscle contractility ($\alpha 1_b$-AR and $\alpha 1_d$-AR) were compared to the effects on prostatic smooth muscle ($\alpha 1_a$-AR). Strips of prostatic tissue and aortic rings were obtained from Long Evans derived male rats weighing 275 grams and sacrificed by cervical dislocation. The prostate tissue was placed under 1 gram tension in a 10 ml bath containing phosphate buffered saline pH 7.4 at 32° C. and isometric tension was measured with force transducers. The aortic tissue was placed under 2 grams tension in a 10 ml bath containing phosphate buffered saline pH 7.4 at 37° C. The ability of test compound to reduce the norepinephrine-induced contractile response by 50% ($IC_{50}$) was determined. Compound 5 inhibited the contractile response in aortic tissue with an $IC_{50}$ of 31.9 $\mu$M and in prostate tissue with an $IC_{50}$ of 1.3 $\mu$M.

Example 17

Select compounds of the invention were tested for their ability to antagonize phenylephrine (PE) induced increases in intraurethral pressure in dogs. The selectivity of these compounds was demonstrated by comparing their effect upon PE induced increases in mean arterial pressure (MAP) in the dog.

Figure 2:
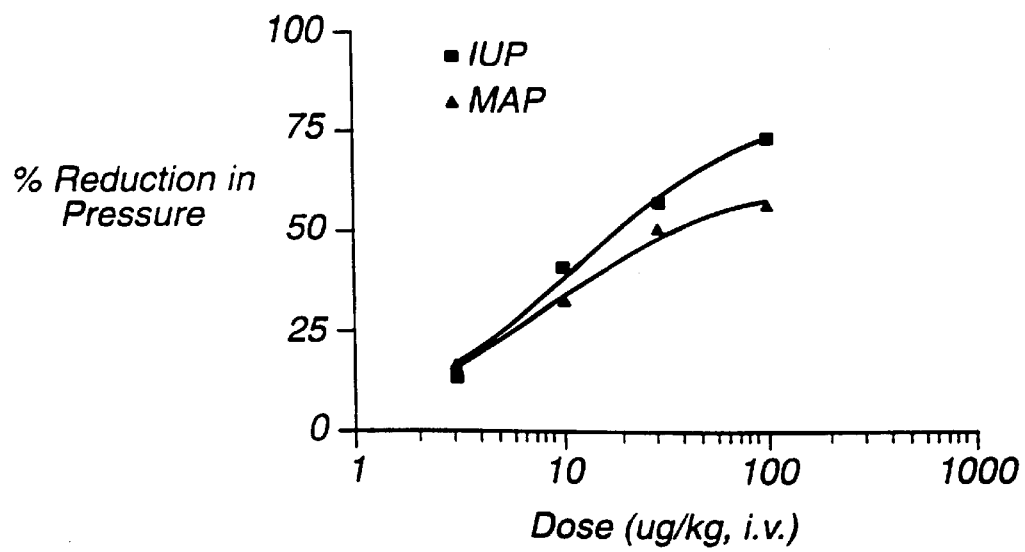
FIG. 2 illustrates the effect of compound 12 on IUP and MAP.

Male beagle dogs were anesthetized and catheterized to measure intraurethral pressure (IUP) in the prostatic urethra. Mean arterial pressure (MAP) was measured using a catheter placed in the femoral artery. Dogs were initially administered six i.v. bolus doses (1 to ≦32 mg/kg) of phenylephrine (PE) to establish a control agonist dose-response curve. IUP and MAP were recorded following each dose until the IUP returned to baseline. The dogs then were given an i.v. bolus dose of the antagonist compound, followed by i.v. PE challenges of ascending doses, as in the control agonist dose-response curve. IUP and MAP measurements following each PE challenge were recorded. The antagonist compound was tested over a dose range of 3 to 300 ug/kg in half-log increments. The interval between antagonist doses was at least 45 minutes and three experiments were performed per dose level for each test compound. FIGS. 1 and 2 illustrates the mean percentage reductions in IUP and MAP for compounds 5 and 12 respectively.

REFERENCES

Breslin D, Fields D W, Chou T-C, Marion D N, Kane M, Vaughan E D, and Felsen D (1993) Medical management of benign prostatic hyperplasia: a canine model comparing the in vivo efficacy of alpha-1 adrenergic antagonists in the prostate. J. Urol. 149: 395–399.

Bruno J F, Whittaker J, Song J, and Berelowitz M. (1991) Molecular cloning and sequencing of a cDNA encoding a human α1A adrenergic receptor. Biochem. Biophys. Res. Commun. 179: 1485–1490.

Bylund D B, Eikenberg D C, Hieble J P, Langer S Z, Lefkowitz R J, Minneman K P, Molinoff P B, Ruffolo R, and Trendelenburg U (1994) IV. International Union of Pharmacology nomenclature of adrenoceptors. Pharmacol. Rev. 46: 121–136.

Carruthers S G (1994) Adverse effects of α1-adrenergic blocking drugs. Drug Safety 11: 12–20.

Faure C, Gouhier C, Langer S Z, and Graham D (1995) Quantification of α1-adrenoceptor subtypes in human tissues by competitive RT-PCR analysis. Biochem. Biophys. Res. Commun. 213: 935–943.

Flavahan N A and VanHoutte P M (1986) α-Adrenoceptor classification in vascular smooth muscle. Trends Pharmacol. Sci. 7: 347–349.

Ford A P D W, Arredondo N F, Blue D R, Bonhaus D W, Jasper J Kava M S, Lesnick J, Pfister J R, Shieh I A, Vimont R L, Williams T J, McNeal J E, Stamey T A, and Clarke D E (1996) RS-17053 (N-[2-(2-Cyclopropylmethoxyphenoxy)ethyl]-5-chloro-a,a-dimethyl-1H-indole-3-ethanamine hydrochloride), a selective α1A-adrenoceptor antagonist, displays low affinity for functional α1-adrenoceptors in human prostate: Implications for adrenoceptor classification. Mol. Pharmacol. 49: 209–215.

Forray C, Bard J A, Wetzel J M, Chiu G, Shapiro E, Tang R, Lepor H, Hartig P R, Weinshank R L, Branchek T A, and Gluchowski C (1994) The α1-adrenergic receptor that mediates smooth muscle contraction in human prostate has the pharmacological properties of the cloned human α1c subtype. Mol. Pharmacol. 45: 703–708.

Gormley G, Stoner E, Bruskewitz R C et al. (1992) The effect of finasteride in men with benign prostatic hyperplasia. N. Engl. J. Med. 327: 1185–1191.

Hatano A, Takahashi H, Tamaki M, Komeyama T, Koizumi T, and Takeda M (1994) Pharmacological evidence of distinct α1-adrenoceptor subtypes mediating the contraction of human prostatic urethra and peripheral artery. Br. J. Pharmacol. 113: 723–728.

Harrison J K, Pearson W R, and Lynch K R (1991) Molecular characterization of α1- and α2-adrenoceptors. Trends Pharmacol. Sci. 12: 62–67.

Hieble J P and Caine M (1986) Etiology of benign prostatic hyperplasia and approaches to pharmacological management. Fed. Proc. 45: 2601–2603.

Hirasawa A, Horie K. Tanaka T, Takagaki K, Murai M, Yano J, and Tsujimoto G (1993) Cloning, functional expression and tissue distribution of human cDNA for the α1c-adrenergic receptor. Biochem. Biophys. Res. Commun. 195: 902–909.

Holck M I, Jones C H M and Haeusler G (1983) Differential interactions of clonidine and methoxamine with postsynaptic α-adrenoceptors of rabbit main pulmonary artery. J. Cardiovasc. Pharm. 5: 240–248.

Lepor H and Rigaud G (1990) The efficacy of transurethral resection of the prostate in men with moderate symptoms of prostatism. J. Urol. 143: 533–537.

Lepor H, Auerbach S, Puras-Baez A et al. (1992) A randomized, placebo-controlled multi/center study of the efficacy and safety of terazosin in the treatment of benign prostatic hyperplasia. J. Urol. 148: 1467–1474.

Lepor H (1995) α-Blockade for benign prostatic hyperplasia (BPH) J. Clin. Endocrinol. Metab. 80: 750–753.

Marshall I, Burt R P, Andersson P O, Chapple C R, Greengrass P M, Johnson G I, and Wyllie M G (1992) Human α1c-adrenoceptor: functional characterisation in prostate. Br. J. Pharmacol. 107 (Proc. suppl. Dec.): 327P.

Marshall I, Burt R P, and Chapple C R (1995) Noradrenaline contraction of human prostate by medicated by α1A-(α1c-)adrenoceptor subtype. Br. J. Pharmacol. 115: 781–786.

Mebust W K, Holtgrewe H L, Cockett A T K, and Peters P C (1989) Transurethral prostatectomy: immediate and postoperative complication. A cooperative study of 13 participating institutions evaluating 3,885 patients J. Urol., 141: 243–247.

Minneman K P, Han C and Abel P W (1988) Comparison of α1-adrenergic receptor subtypes distinguished by chloroethylclonidine and WB41 01. Mol. Pharmacol. 33: 509–514.

Minneman K P and Esbenshade T A (1994) α1-Adrenergic receptor subtypes. Annu. Rev. Pharmacol. Toxicol. 34:117–133.

Morrow A L and Creese I (1986) Characterization of alpha 1-adrenergic receptor subtypes in rat brain: A reevaluation of [3H]WB4104 and [3H]prazosin binding. Mol. Pharmacol. 29: 321–330.

Muramatsu I (1992) A pharmacological perspective of α1-adrenoceptors: subclassification and functional aspects, in α-Adrenoceptors (Fujiwara M, Sugimoto T, and Kogure K, eds.). Excerpta Medica Ltd., Tokyo, 193–202.

Muramatsu I, Oshita M. Ohmura T, Kigoshi S. Akino H, Gobara M. and Okada K (1994) Pharmacological characterization of α1-adrenoceptor subtypes in the human prostate: functional and binding studies. Br. J. Urol. 74: 572–577.

Oesterling J E (1995) Benign prostatic hyperplasia. Medical and minimally invasive treatment options. N. Engl. J. Med. 332: 99–109.

Price D T, Lefkowitz R J, Caron M G, Berkowitz D, and Schwinn D A (1994) Localization of mRNA for three distinct α1-adrenergic receptor subtypes in human tissues: implications for human α-adrenergic physiology. Mol. Pharmacol. 45:171–175.

Ramarao C S, Kincade Denker J M, Perez D M, Gaivin R J, Riek R P, and Graham R M (1992) Genomic organization and expression of the human α1B-adrenergic receptor. J. Biol. Chem. 267: 21936–21945.

Schwinn D A, Johnston G I, Page S O, Mosley M J, Wilson K H, Worman N P, Campbell S, Fidock M D, Furness L M, Parry-Smith D J, Peter B, and Bailey D S (1995) Cloning and pharmacological characterization of human alpha-1 adrenergic receptors: sequence corrections and direct comparison with other species homologues. JPET 272:134–142.

Weinberg D H, Trivedi P, Tan C P, Mitra S, Perkins-Barrow A, Borkowski D, Strader C D, and Bayne M (1994) Cloning, expression and characterization of human α adrenergic receptors α1A, α1B, and α1C. Biochem. Biophys. Res. Commun. 201: 1296–1304.

Weis K A, Epstein R S, Huse D M, Deverka P A and Oster G (1993) The costs of prostatectomy for benign prostatic hyperplasia. Prostate 22: 325–334.

Wennberg J E, Roos N, Sola L, Schori A, and Jaffe R (1987) Use of claims data systems to evaluate health care outcomes: mortality and reoperation following prostatectomy. JAMA 257: 933–936.

Yamada S, Tanaka C, Kimura R, and Kawabe K (1994) Alpha 1-adrenoceptors in human prostate: characterization and binding characteristics of alpha 1-antagonists. Life Sci. 54: 1845–1854.

What is claimed is:

1. A compound of Formula II wherein:

A is $(CH_2)n$ where n is 1–6;

$R_1$ is branched $C_{3-6}$alkyl, phenyl,
   substituted phenyl
      where the phenyl substituents are independently selected from one or more of the group consisting of $C_{1-5}$alkyl, $C_{1-5}$alkoxy and halogen,
   phenyl$C_{1-5}$alkyl, or
   substituted phenyl$C_{1-5}$alkyl
      where the phenyl substituents are independently selected from one or more of the group consisting of $C_{1-5}$alkyl, $C_{1-5}$alkoxy and halogen;

$R_7$ is CBZ.

2. The compounds of claim 1 where n is 2–4 and $R_1$ is branched $C_{3-6}$alkyl.

3. The compound of claim 1 wherein n is 2 and $R_1$ is isopropyl.

* * * * *